US007444245B2

(12) United States Patent
Pfeiffer et al.

(10) Patent No.: US 7,444,245 B2
(45) Date of Patent: Oct. 28, 2008

(54) FIELD DEVICE FOR DETERMINING AND/OR MONITORING A PROCESS VARIABLE

(75) Inventors: Helmut Pfeiffer, Steinen (DE); Sergej Lopatin, Lörrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 0 days.

(21) Appl. No.: 10/563,964

(22) PCT Filed: Jul. 8, 2004

(86) PCT No.: PCT/EP2004/007462

§ 371 (c)(1),
(2), (4) Date: Jul. 5, 2006

(87) PCT Pub. No.: WO2005/008190

PCT Pub. Date: Jan. 27, 2005

(65) Prior Publication Data

US 2007/0021931 A1    Jan. 25, 2007

(30) Foreign Application Priority Data

Jul. 11, 2003  (DE) .................................. 103 31 730

(51) Int. Cl.
*G01N 11/00* (2006.01)
*G01F 23/00* (2006.01)
*G01L 7/00* (2006.01)

(52) U.S. Cl. .............................. 702/54; 702/48; 702/56; 702/137; 702/138; 73/54.26; 73/54.27; 73/54.41; 73/702

(58) Field of Classification Search .................. 702/48, 702/50, 51, 54–56, 137, 138; 73/54.23–54.29, 73/54.31–54.38, 54.41, 61.45, 61.75, 64.43, 73/570, 579, 592, 662, 149, 170.13, 861.18, 73/861.19, 290 V, 702–704, 19.03, 24.01, 73/24.05, 30.01, 30.04, 31.05, 32 A, 61.49, 73/61.79, 64.53; 700/281–285
See application file for complete search history.

(56) References Cited

U.S. PATENT DOCUMENTS 4,815,323 A * 3/1989 Ellinger et al. ............ 73/290 V (Continued)

FOREIGN PATENT DOCUMENTS

DE         24 05 991       8/1974

(Continued)

*Primary Examiner*—Manuel L Barbee
(74) *Attorney, Agent, or Firm*—Bacon & Thomas, PLLC

(57) ABSTRACT

Field device for determining and/or monitoring at least one process variable of a medium in a container. The field device includes: at least one mechanically oscillatable unit connected with the container via a process connection; and at least one driver/receiver unit, which excites the mechanically oscillatable unit to oscillate, or detects the oscillations of the mechanically oscillatable unit, as the case may be. The invention includes that the mechanically oscillatable unit has at least three oscillatory members, that at least one oscillatory member is connected with the process connection at an attachment region, that the three oscillatory members can execute oscillations, which the driver/receiver unit produces, or detects, as the case may be, and that the three oscillatory members are embodied and interconnected in such a manner and the attachment region is selected in such a manner, that an approximately defined transfer of reaction forces and reaction torques occurs between the mechanically oscillatable unit and the process connection.

13 Claims, 4 Drawing Sheets

U.S. PATENT DOCUMENTS

| | | | | |
|---|---|---|---|---|
| 4,975,615 | A | * | 12/1990 | Katahara ..................... 310/328 |
| RE33,837 | E | * | 3/1992 | Chung et al. .................. 367/31 |
| 5,138,886 | A | * | 8/1992 | Tilley, Sr. .................... 73/749 |
| 6,360,175 | B1 | * | 3/2002 | Cunningham et al. ......... 702/56 |
| 6,449,566 | B1 | * | 9/2002 | Oeschger ..................... 702/54 |
| 2005/0086012 | A1 | * | 4/2005 | Lapinski et al. ............... 702/48 |

FOREIGN PATENT DOCUMENTS

| | | |
|---|---|---|
| DE | 31 43 515 A1 | 5/1983 |
| EP | 0 499 265 B1 | 5/1995 |
| EP | 0 848 237 A1 | 6/1998 |
| EP | 0 940 658 A1 | 9/1999 |

* cited by examiner

FIELD DEVICE FOR DETERMINING AND/OR MONITORING A PROCESS VARIABLE

FIELD OF THE INVENTION

The invention relates to a field device for determining and/or monitoring at least one process variable of a medium in a container. The field device includes: At least one mechanically oscillatable unit, which is connected with the container via a process connection; and at least one driver/receiver unit, which excites the mechanically oscillatable unit to oscillate, or which detects the oscillations of the mechanically oscillatable unit, as the case may be. Examples of the process variable are fill level, density or viscosity of a medium.

BACKGROUND OF THE INVENTION

The principle of operation of such a field device is that the oscillation of an oscillatable unit depends on whether it is oscillating freely or covered by the medium—this is then the fill level determination—or whether, for example, the viscosity of the medium changes—this is then e.g. the monitoring of viscosity. Depending on a property of the medium, or, in general, whether the medium is covering the oscillatable unit, or not, the frequencies and amplitudes of the oscillations will differ. Working backwards from a frequency change, thus, allows, for example, in the case of application as a fill-level sensor, the conclusion that the medium has exceeded, or subceeded (or fallen beneath), a certain fill level, as determined by the installed position of the sensor. The same holds also for the amplitude.

The assignee manufactures and sells oscillating forks under the mark LIQUIPHANT, e.g. for fill level detection. The advantage of oscillating forks lies in the fact that the oscillations of the two fork tines exactly compensate, or cancel, so that e.g. no energy of the fork is transferred to the region of attachment, thus to the area where the measuring device is connected to the container, and, from there, into the container itself. For types of application in which it is possible, for example, that material can get stuck between the tines, it is of interest to use so-called single-rod devices. In this case, the inherent canceling of the forces is lacking, and, consequently, forces and torques can act on the attachment.

SUMMARY OF THE INVENTION

Thus, it is an object of the invention to provide for a field device a mechanically oscillatable unit, whose oscillations result in little, or no, forces and torques on the attachment.

The object is achieved, according to the invention, by the following combination of features: The mechanically oscillatable unit has at least three oscillatory members; at least one oscillatory member is connected to the process connection at a region of attachment; the three oscillatory members execute oscillations, which the driver/receiver unit produces, or detects, as the case may be; and the three oscillatory members are embodied and interconnected in such a manner, and the region of attachment is selected in such a manner, that an approximately defined transfer of reaction forces and reaction torques occurs between the mechanically oscillatable unit and the process connection. A basic idea of the invention is thus that the mechanically oscillatable unit is composed of three oscillatory members. Two thereof are connected with the third oscillatory member. This means that the oscillations are also directly coupled together, e.g. between interconnected pairs of oscillatory members, or indirectly, as the case may be. Thus, also forces and torques are transferred between one another. The construction of the oscillatory members can, in such case, be rod-shaped or tubular, but, also, e.g. spheres connected with appropriate springs can be involved, or rectangularly-shaped structures. The oscillatory members can be made of the same, or of different, materials, e.g. metal or plastic. Essential are the physical variables relevant for oscillation, such as stiffness and mass. With reference to the frequency of oscillation and the amplitude, naturally also length is relevant. The matching of the lengths should, naturally, be such that the oscillations do not mutually interfere.

An embodiment includes that the oscillations of the mechanically oscillatable unit are bending oscillations. An alternative label for bending oscillations is transverse oscillations. Such oscillations are used in the above-mentioned LIQUIPHANT instruments manufactured and sold by the assignee for fill level detection. In this embodiment, the oscillations are, for example, not ultrasonic oscillations.

An advantageous embodiment provides that at least the embodiment of the three oscillatory members, their connections with one another and at the region of attachment, and their matching to one another are determinable and/or calculable in such a manner that at least the reaction forces and reaction torques acting on the process connection as a result of the oscillations of the mechanically oscillatable unit are as close as possible to zero. The oscillatory members of the mechanically oscillatable unit and the selection of the attachment region can be matched to one another by appropriate calculations or by experiment. The choice of the attachment region, thus where an oscillation element is connected with the process connection, is relevant, because such oscillation element likewise oscillates, i.e. there are areas of this oscillatory element that are continually in motion and, therefore, can not serve for the connection with the process connection, in so far as the attachment region is to remain at rest. By the use of three oscillatable members, an increase of the degrees of freedom results, so that a balancing of the forces and torques becomes quite possible. Advantageously, the one oscillation element is connected with the process connection, where such element exactly has an oscillation node, thus a region that does not move during oscillation. This embodiment has, consequently, the advantage that the oscillations do not affect the container.

An advantageous embodiment provides that the three oscillatory members are a long rod of length L, mass M and stiffness EI, a first short rod of length L1, mass M1 and stiffness EI1, and a second short rod of length L2, mass M2 and stiffness EI2, that the first short rod is connected, with an end region turned toward the process, to the long rod, to the long rod, at an end region of the long rod turned toward the process, that the second short rod is connected, with an end region turned away from the process, to the long rod, at an end region of the long rod turned away from the process, and that the long rod is connected with the process connection at least at an attachment region. A basic idea is, thus, that an, overall, single-rod construction is used, with such being composed of one long rod and two short rods, with all three units being able to oscillate. The short rods are each connected at one end with the long rod and have, preferably, a free end, which is not connected with the long rod and which can, therefore, oscillate freely. Such a rod-shaped, or tubular, embodiment simplifies calculation of the torques and forces and, consequently, makes the concrete implementation clearer. The connecting of the short rods with the long rod can, in such case, occur directly e.g. by the screwing of the short rods into correspondingly embodied holes in the long rod, or indirectly e.g. via a spring element. The connection can, furthermore, be effected directly at the ends of the respective end regions or at a lateral section thereof. It is also possible to have a short rod extend slightly beyond the long rod. Other embodiments are possible.

An advantageous embodiment provides that both short rods have essentially equal length, essentially equal mass, essentially equal mass moment of inertia about their center of rotation, and essentially equal stiffness. This is the simplest embodiment, with which the two short rods oscillate with opposite phase and can exactly cancel one another.

An advantageous embodiment includes that the first and/or the second short rod have/has at least one groove/neck, which determines at least the oscillation frequency of the mechanically oscillatable unit. Such a groove/neck effects the rotational stiffness of the corresponding short rod and permits, consequently, a tuning of the resonant frequency dependent thereon.

An advantageous embodiment provides, that the long rod coaxially surrounds at least the first short rod. Consequently, at least only the long rod comes in contact with the medium, and the first short rod oscillates always under the same physical conditions. This oscillation of the first short rod is, therefore, also not influenced by accretions on, or corrosion of, the long rod. A further embodiment provides that the long rod coaxially surrounds both short rods. Such a mechanically oscillatable unit is then optimally self-contained and protected from the environment, so that, also, no medium can penetrate. From the outside, then it appears to be only one oscillating unit. The embodiment as long rod, or, more specifically, long tube, has, in such case, the advantage that the forces acting through the material, in most cases—excepting special exceptions at e.g. very high loading—do not lead to deformation.

An advantageous embodiment includes that at least the second short rod coaxially surrounds the long rod. In connection with the above-mentioned embodiment, this means that the long rod surrounds the first short rod at the end turned toward the process and itself, in turn is surrounded at the other end by the second short rod. The second short rod can, in such case, coaxially surround the long rod over the complete length of the second short rod; the second short rod can, however, also surround the long rod only partially and e.g. protrude with its end turned away from the process, beyond the long rod. This embodiment has advantages concerning how to put such into practice from a manufacturing point of view. First, the first short rod is secured in the long rod. Then, the tubular, long rod, which is, for example, open on the end turned away from the process, is connected with the second short rod. The second short rod can, in such case, also be open below, so that, for example, there is still always an open access to the interior of the long rod. This is advantageous for the possible running of cables.

An advantageous embodiment includes that the process connection is a tube, to which the long rod is secured, at least in the attachment region.

The great advantage lies in the fact that at least the section of the long rod turned away from the process can, it is true, oscillate, yet it is protected, however, for example, from deposition of accretions, from corrosion, or, in general, from the medium and the process conditions reigning in the container. Furthermore, the region located directly in the container, which, thus, acts there as a "disturbance", is shortened.

An advantageous embodiment provides that the driver/receiver unit is located between the end region of the long rod turned toward the process and the end region of the first short rod turned toward the process. A further advantageous embodiment provides that the driver/receiver unit is located between the end region of the long rod turned away from the process and the end region of the second short rod turned away from the process. The one short rod is, in both embodiments, this connected with the oscillation exciter, or detector, as the case may be, and the then other short rod serves as compensation-mass, or-oscillator.

An embodiment includes that at least one piezoelectric element is provided in the driver/receiver unit. This is an embodiment which is usual for a driver/receiver unit in vibronics.

An advantageous embodiment provides that the piezoelectric element in the driver/receiver unit has at least two segments, which are polarized in mutually opposite directions, with the polarization directions lying parallel to an axis of rotation of the mechanically oscillatable unit. Such an element has the advantage that a tilting torque is produced directly, since one segment is contracted, and the other segment expanded, by an applied voltage. Such a tilting torque is required, above all, for producing bending oscillations in the oscillatable unit.

BRIEF DESCRIPTION OF THE DRAWINGS

The invention will now be explained in greater detail on the basis of the appended drawings, the figures of which show as follows.

DETAILED DESCRIPTION

Figure 1:
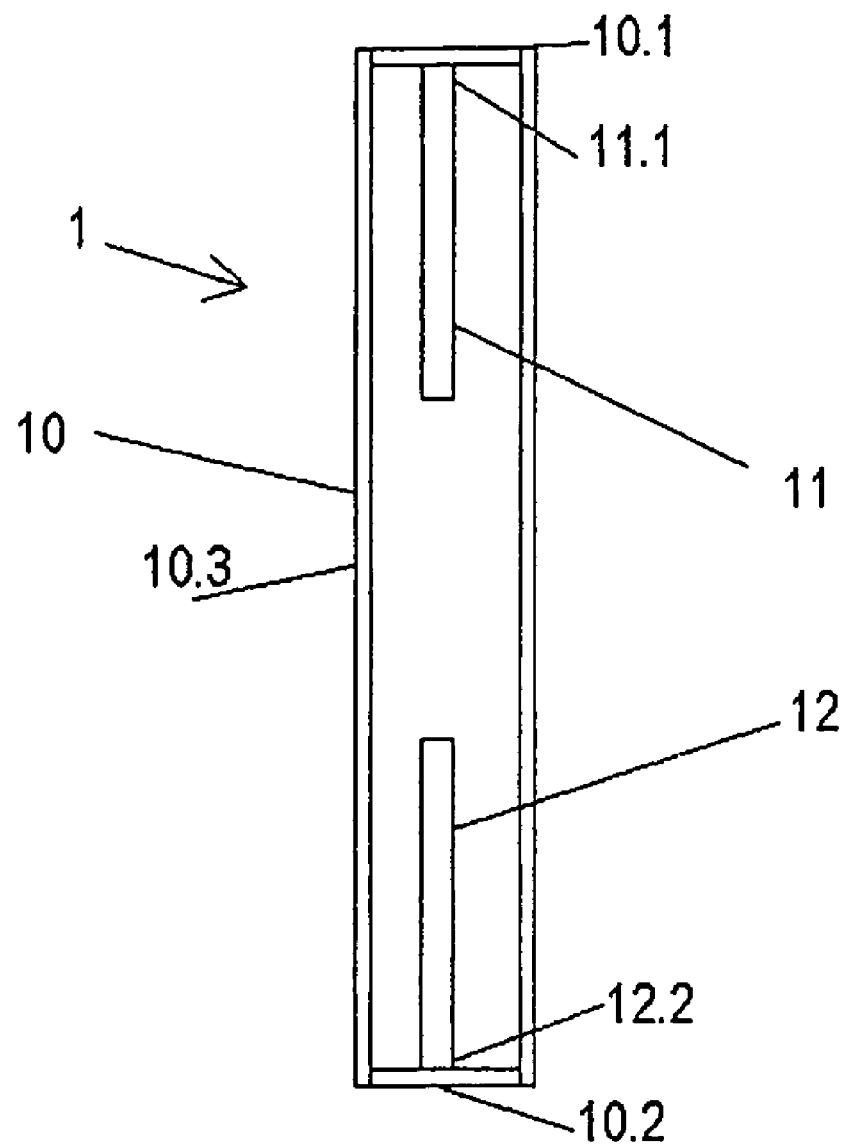
FIG. 1 the structure, in principle, of the mechanically oscillatable unit.

FIG. 1 shows the construction, in principle, of the mechanically oscillatable unit 1. The long rod 10 is embodied, in this case, such that it surrounds the two short rods 11, 12 coaxially. Alternative embodiments are, however, possible. The first short rod 11 is connected, at its end region 11.1 turned toward the process, with the end region 10.1 of the long rod 10 turned toward the process. Due to the nearness to the medium, it is advantageous, when the first short rod 11 is arranged in the long rod 10, since, then, only one component—namely the long rod 10—can come in contact with the medium. At the end region 10.2 of the long rod 10 turned away from the process, the long rod is connected with the second short rod 12, at the end region 12.2 of the second short rod turned away from the process. The other end regions of the short rods 11, 12 are, in each case, free ends, which can freely oscillate. In the attachment region 10.3, the long rod 10 is connected with the process connection 2. In such case, the process connection can be a nipple fitting, which is screwed into an opening of the container (not shown). Then, even in the case of buildup of accretions of the medium on the long rod 10, the two short rods 11, 12 are still able to execute oscillations of opposite phase and, so, to prevent that forces or torques act on the attachment.

Figure 2:
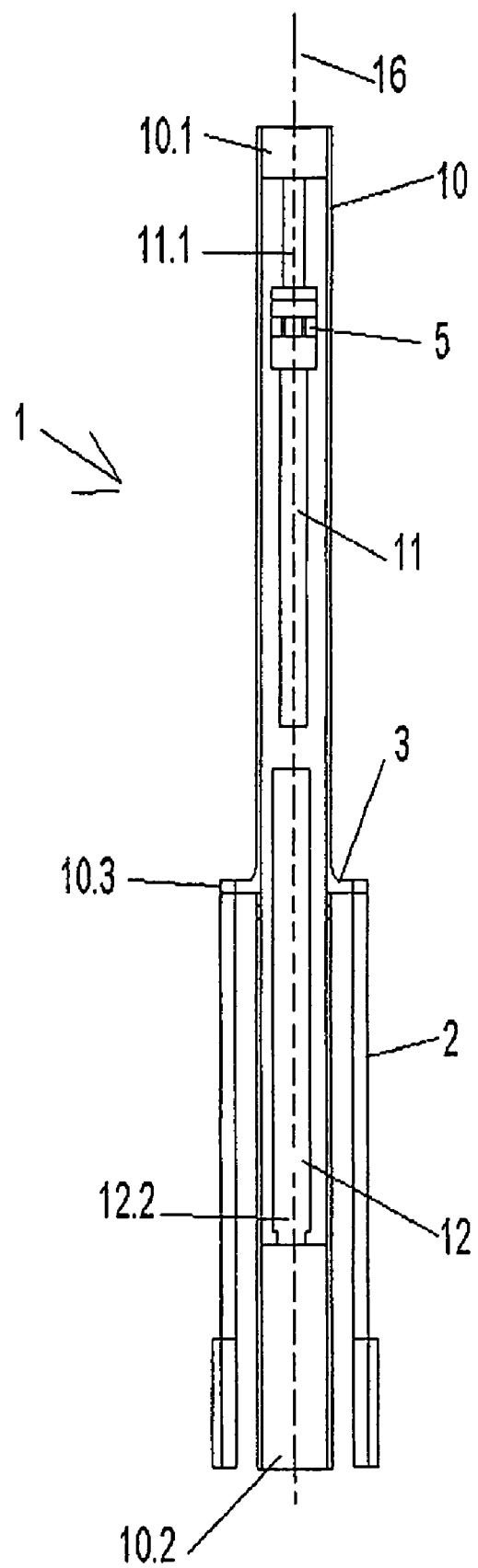
FIG. 2 a detailed illustration of the mechanically oscillatable unit, with the piezo unit being in the direction of the process.

FIG. 2 is a more detailed embodiment of the mechanically oscillatable unit 1. The driver/receiver unit 5 is located in the direction of the process, between the end region 11.1 of the first short rod 11 turned toward the process and the corresponding end region 10.1 of the long rod 10. The driver/receiver unit 5 is shown here schematically as a piezoelectric element, which has at least two segments of mutually opposing polarizations. These polarizations are parallel to an axis 16 of rotation of the oscillatable unit 1. Such an embodiment has the advantage, that, upon application of a voltage to this piezoelectric element, one segment contracts, while the other expands. Therefore, a tilting movement is directly produced, which leads to bending oscillations in the mechanically oscillatable unit 1. The long rod 10 is connected with the process connection 2 at the attaching region 10.3. This connection 2 is associated with a sealing fitting 3, so that no material can penetrate into the interior of the mechanically oscillatable unit 1. In the figure, also well recognizable is the fact that only the region between the attachment region 10.3 and the end region 10.1 of the long rod 10 turned toward the process can come into contact with the process, while, nevertheless, the entire length of the long rod 10 is oscillatable.

Figure 3:
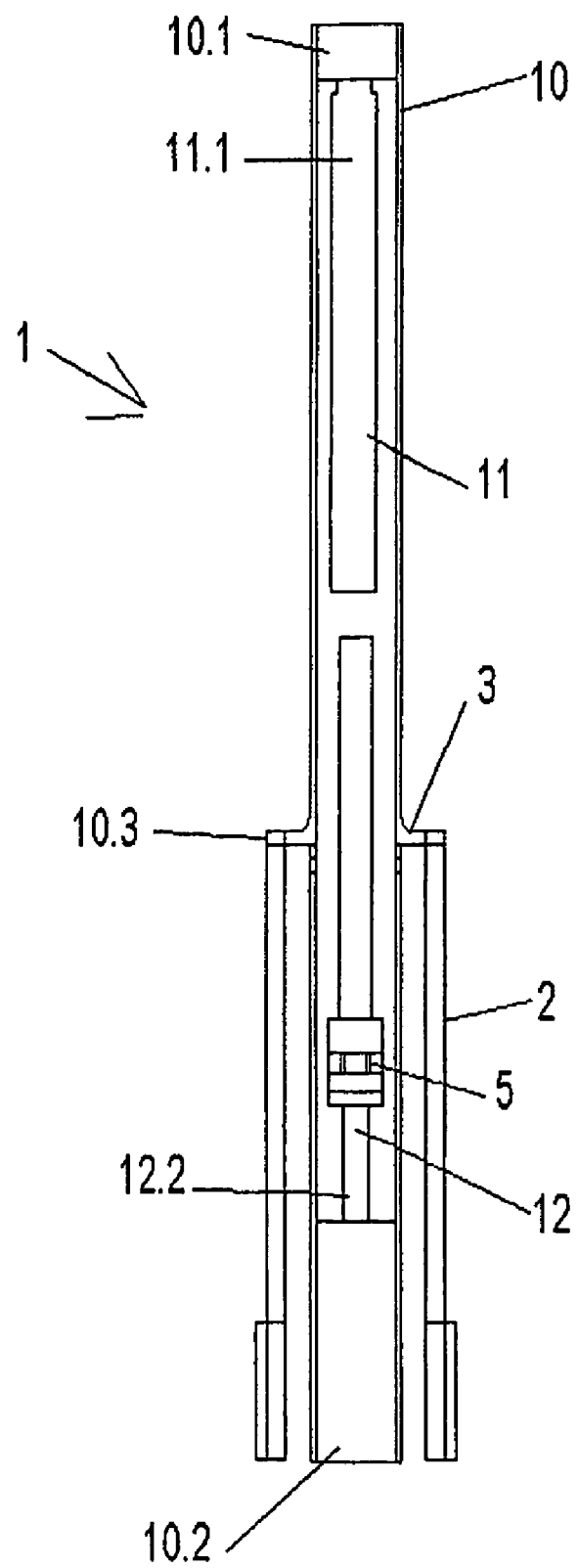
FIG. 3 an embodiment, in which the piezo unit is located in the end turned away from the process.

FIG. 3 presents an embodiment like that in FIG. 2, where, however, the driver/receiver unit 5, in this case, lies between the end region 12.2 of the second short rod 12 turned away from the process and the corresponding end region 10.2 of the long rod 10.

Figure 4:
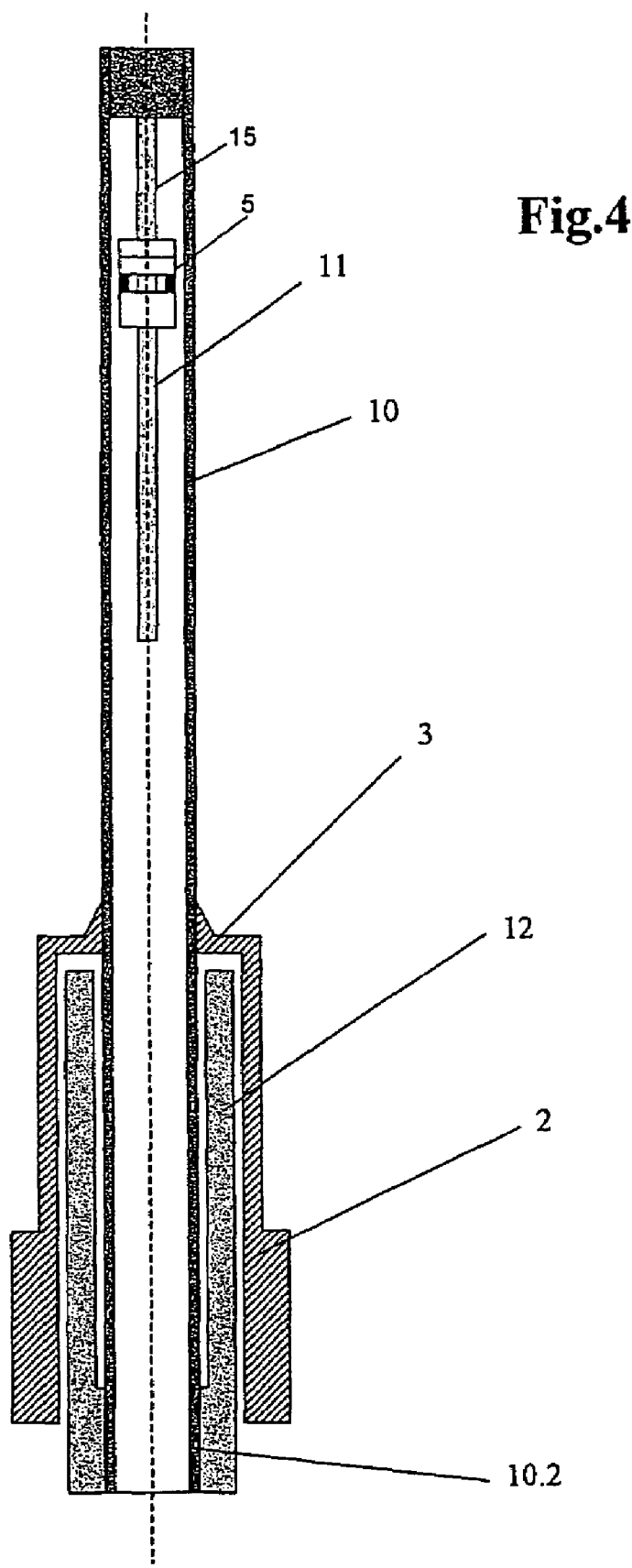
FIG. 4 a variation on the embodiment of FIG. 2.

FIG. 4 shows an alternative embodiment, as compared to that in FIG. 2. Here, the driver/receiver unit 5 is again in the first short rod 11. But, the second short rod 12 is now embodied as a tube, whose inner diameter is greater than the outer diameter of the long rod 10. Consequently, the second rod 12 can coaxially surround the long rod 10. If such a short rod 12 is connected with the long rod 10 by a force, or shrink, fit, then the unconnected part turned toward the process—thus the, in effect, free end—can oscillate freely. In this special embodiment, the second short rod 12 coaxially surrounds the long rod 10—the long rod is, in effect, surrounded, at its end turned away from the process, by a beaker-shaped object (which, if required, can also have one or more openings in its bottom)—and, in turn, the long rod 10 coaxially surrounds the first short rod 11. Also in this embodiment, with appropriate tuning, the two short rods 11, 12 and the long rod 10 execute oscillations of opposite phase, such that the forces and torques acting on the sealing fitting 3 and the connection 2 are opposite and equally large, so that no net reaction forces and reaction torques act on the sealing fitting 3 and the connection 2. Also shown in this FIG. 4 is that the groove/neck 15 can also extend over a greater section. The first short rod 11 is composed of two sections: One section is located between the driver/receiver unit 5 and the connection site of the long rod 10 and the first short rod 11 and the second section is located on the other side of the driver/receiver unit 5. The section in the direction of the process has a lesser diameter and, thus, is, in effect, an extended neck 5.

The invention claimed is:

1. A field device for determining and/or monitoring at least one process variable of a medium in a container, comprising:
   at least one mechanically oscillatable unit connected with the container via a process connection, said mechanically oscillatable unit has at least three oscillatory members;
   at least one oscillatory member is connected, at an attachment region, with the process connection; and
   at least one driver/receiver unit, wherein:
   said driver/receiver unit excites said mechanically oscillatable unit to oscillate, and/or said driver/receiver unit detects the oscillations of said mechanically oscillatable unit;
   said three oscillatory members execute oscillations, which said driver/receiver unit produces, and/or detects;
   said three oscillatory members comprise a long rod of length (L), mass (M) and stiffness (EI), a first short rod of length (L1), mass (M1) and stiffness (EI1) and a second short rod of length (L2), mass (M2) and stiffness (EI2); said first short rod is connected, with an end region turned toward the process, to said long rod, at an end region of said long rod turned toward the process; said second short rod is connected, with an end region turned away from the process, to said long rod, at an end region of said long rod turned away from the process; and said long rod is connected with the process connection at least at an attachment region; and
   said three oscillatory members are embodied and interconnected in such a manner, and said attachment region is selected in such a manner, that an approximately defined transmission of reaction forces and reaction torques occurs between said mechanically oscillatable unit and the process connection.

2. The field device as claimed in claim 1, wherein:
the oscillations of said mechanically oscillatable unit are bending oscillations.

3. The field device as claimed in claim 1, wherein:
at least the embodiment of said three oscillatory members, their interconnections, and said attachment region and their matching to one another are determinable and/or calculable in such a manner that at least the net reaction forces and reaction torques acting on said process connection because of the oscillations of said mechanically oscillatable unit are as close to zero as possible.

4. The field device as claimed in claim 1, wherein:
said two short rods have essentially equal length, essentially equal mass, or essentially equal mass moment of inertia about their center of rotation, as the case may be, and essentially equal stiffness.

5. The field device as claimed in claim 1, wherein:
said first and/or said second short rod have/has at least one groove/neck, which determines at least the oscillation frequency of said mechanically oscillatable unit.

6. The field device as claimed in claim 1, wherein:
said long rod surrounds at least said first short rod coaxially.

7. The field device as claimed in claim 1, wherein:
at least said second short rod coaxially surrounds said long rod.

8. The field device as claimed in claim 1, wherein:
said long rod coaxially surrounds both of said short rods.

9. The field device as claimed in claim 1, wherein:
said process connection is a tube, to which said long rod is secured at least in the attachment region.

10. The field device as claimed in claim 1, wherein:
said driver/receiver unit is located between the end region of said long rod turned toward the process and the end region of said first short rod turned toward the process.

11. The field device as claimed in claim 1, wherein:
said driver/receiver unit is located between the end region of said long rod turned away from the process and the end region of said second short rod turned away from the process.

12. The field device as claimed in claim 1, further comprising:
at least one piezoelectric element provided in said driver/receiver unit.

13. The field device as claimed in claim 12, wherein:
said piezoelectric element in said driver/receiver unit includes at least two segments, which are polarized in mutually opposite directions, wherein the polarization directions lie parallel to an axis of rotation of said mechanically oscillatable unit.

* * * * *